United States Patent
Crunaire et al.

(10) Patent No.: US 9,018,016 B2
(45) Date of Patent: Apr. 28, 2015

(54) MATERIAL AND METHOD FOR TRAPPING, DETECTING AND QUANTIFYING HETEROCYCLIC AROMATIC COMPOUNDS AND OTHERS

(75) Inventors: Sabine Crunaire, Douai (FR); Thu-Hoa Tran-Thi, Saint Fargeau-Ponthierry (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 13/508,702

(22) PCT Filed: Nov. 10, 2010

(86) PCT No.: PCT/EP2010/067227
§ 371 (c)(1),
(2), (4) Date: Jul. 31, 2012

(87) PCT Pub. No.: WO2011/058066
PCT Pub. Date: May 19, 2011

(65) Prior Publication Data
US 2012/0295363 A1 Nov. 22, 2012

(30) Foreign Application Priority Data
Nov. 10, 2009 (FR) .................................... 09 57919

(51) Int. Cl.
| | | |
|---|---|---|
| G01N 21/78 | (2006.01) | |
| G01N 21/00 | (2006.01) | |
| G01N 31/22 | (2006.01) | |
| G01N 31/00 | (2006.01) | |
| G01N 21/77 | (2006.01) | |

(52) U.S. Cl.
CPC ................ G01N 31/22 (2013.01); G01N 21/78 (2013.01); G01N 2021/7786 (2013.01)

(58) Field of Classification Search
CPC ....... G01N 21/78; G01N 21/00; G01N 31/22; G01N 31/00; G01N 2021/7786; G01N 2021/7769; G01N 2021/77; G01N 2021/75; G01N 2021/00
USPC ....................................................... 436/96, 91
See application file for complete search history.

(56) References Cited

FOREIGN PATENT DOCUMENTS

| FR | 2 890 745 A1 | 3/2007 |
| JP | 200625883 A | 9/2006 |
| WO | 2006/107370 A1 | 10/2006 |

OTHER PUBLICATIONS

Wood, et al., "Indole and 3-chloroindol: The source of the disagreeable odor of *Hygrophorus paupertimus*", Mycologia, 2003, 95(5), pp. 807-808.

(Continued)

*Primary Examiner* — Christine T Mui
(74) *Attorney, Agent, or Firm* — Knobbe, Martens, Olson & Bear, LLP

(57) ABSTRACT

What is provided includes a porous sol-gel material whose intrinsic pH is lower than 1 and comprising at least one probe molecule chosen from the group consisting of croconic acid, p-dimethyl-aminobenzaldehyde (DMABA), p-dimethyl aminocinnamaldehyde (DMACA), p-methoxybenzaldehyde (MOB) and 4-methoxy-1-naphtaldehyde (MON). In addition, a detection system containing the porous sol-gel material and a method of preparation and use of the porous sol-gel material for trapping and/or detecting and optionally quantifying at least one chemical compound such as indole and indole compounds are provided.

19 Claims, 4 Drawing Sheets

(56) References Cited

OTHER PUBLICATIONS

Curioni, et al, "Key odorants in various cheese types as determined by gas chromatography-olfactometry", 2002, International Dairy Journal, vol. 12, pp. 959-984.

Lombard, et al., "Comparison of Three Reagents for Detecting Indole Production by Anaerobic Bacteria in Microtest Systems", Journal of Clinical Microbiology, Sep. 1983, vol. 18, No. 3, pp. 609-613.

Miller, et al., "Spot Indole Test: Evaluation of Four Reagents", Journal of Clinical Microbiology, Apr. 1982, vol. 15, No. 4, pp. 589-592.

Turner, "A New Reagent for the Assay of Indole in the Tryptophanase Reation", 1961 Biochemical Journal, 1961, vol. 78, pp. 790-792.

Kohno, et al., "Color Sensors for Indole Vapors Based on Ehrlich-type Reactions", Analytical Sciences, Jan. 2009, vol. 25, pp. 129-132.

Volkl, et al., "Neue Method zum Nachweis von Indolderivaten: New Colour Reaction to Identify Indoles", Arztl. Lab, 1973, vol. 19, pp. 45-50, English translation thereof.

Qureshi, et al., "A Sensitive and Selective Resin Spot Test for Diphenylamine", Analytical Chemistry, Dec. 1966, vol. 38 (13), pp. 1956-1958.

Durkee, et al., "The Detection of Some Indoles and Related Compounds on Paper Chromatograms", Journal of Chromatology, 1964, vol. 13, pp. 173-180.

Vracko, et al., "Indole-Spot Test in Bacteriology", American Journal of Clinical Pathology, Apr. 1963, vol. 39, No. 4, pp. 429-432.

Kohno, et al., "Visual Color Sensor for Indole Vapors", Chemistry Letters, 2007, vol. 36, No. 1, pp. 98-99.

Preliminary Search Report issued on Jun. 23, 2010 for French Application No. 0957919. All the references cited in the research report have bee submitted on May 8, 2012.

Ingersoll, et al., "Using sol-gel-based platforms for chemical sensors", Chemtech, Washington, DC, US, vol. 27, No. 1, Jan. 1, 1997, pp. 26-31, XP002060846.

Gojon, et al., "A comparison of immobilization sol-gel methods for an optical chemical hydrazine sensor", Sensors and Actuators B, Elsevier Sequoia S.A., Lausanne, CH LNKD-DOI:10.1016/S0925-4005(97) 80186-4, vol. 38, No. 1-3, Jan. 1, 1997, pp. 154-162, XP004083686.

International Search Report and Written Opinion issued on Jan. 21, 2011 for International Patent Application No. PCT/EP2010/067227.

MATERIAL AND METHOD FOR TRAPPING, DETECTING AND QUANTIFYING HETEROCYCLIC AROMATIC COMPOUNDS AND OTHERS

RELATED APPLICATIONS

This application is a U.S. National Phase of International Application No. PCT/EP2010/067227, filed Nov. 10, 2010, designating the U.S., and published in French as WO 2011/058066 on May 19, 2011 which claims the benefit of French Patent Application No. 09 57919 filed Nov. 10, 2009.

TECHNICAL FIELD

The present invention belongs to the field concerning the detection and optionally the quantification of compounds of interest such as heterocyclic aromatic compounds.

More specifically, the present proposes a device and a method capable of detecting and optionally of quantifying heterocyclic aromatic compounds such as indole and the derivatives thereof.

BACKGROUND

Indole compounds and more particularly indole and skatole can be produced by sources of different type. The most important source for indole is the development of micro-organisms. Indeed, when they grow, bacteria having the tryptophanase enzyme produce indole from the tryptophan contained in a nutrient medium. For example, in the field of biochemistry and microbiology, the detection of indole is a well-known means for determining a taxonomic classification of micro-organisms. This differentiation is important firstly from an <<epidemiological>> standpoint, and secondly on account of the differences in sensitivity to antibiotics of the different bacterial strains.

In the agri-food sector, the detection of indole allows the determination of the freshness of sea produce (shrimps, shellfish, etc.). Indole can effectively be considered to be an indirect factor indicating the bacterial load of products and therefore the state of advance of the decomposition thereof. In this same field, the detection of indole is also important for the marketing of meat, in particular pork or lamb. Indeed, meat may, in some cases, have a strong sickening smell on cooking and prevent the consumption thereof. This smell derives from indole and skatole which have accumulated in the adipose tissue and the smell of which is perceived when the cooking temperature rises. The combined detection of indole and skatole in milk or meat can also be used as a mode for tracing the type of cattle feed (grass, food concentrate). In addition, studies have also shown that a high indole content in cattle feed could be a triggering factor of pulmonary emphysema.

In the field of veterinary screening, the evidencing of a large amount indole in cow milk is sufficient evidence that the cow under consideration suffers from mastitis [1].

Indole is also an active compound used in some pesticides as an attraction odour identical to the odour produced by the pheromones of some insects such as the chrysomelid corn rootworm and beetles, etc. Therefore the detection of indole must be able to be used as a way of monitoring the dose of sprayed insecticide and this, as part of health and environmental inspections. Again in the field of environmental control, and more particularly the quality of waste water derived from intensive farming, cosmetic industries or chemical industries, it is important to determine the content of indole since it is extremely toxic for aquatic organisms.

In the field of health inspections, the detection of indole and skatole may be of interest for evidencing the presence of some types of fungi (*H. paupertinus, Tricholoma bufonium, T. inamoenum, T. lascivum, T. sulphureum, Boletus calopus*, etc.) [2]. This could allow the classifications for example of edible or poisonous species, detections of mould in indoor air responsible for lung diseases and allergies, or even maturation tests for cheese production, indole and skatole being found in cheeses such as mozzarella, Emmenthal cheese, Hervé or Limburger cheese [3].

Finally, in the perfume, cosmetics and flavouring fields, indole is used in very low concentration as a fragrant component (flower, jasmine scent).

From the foregoing it is clear that the detection and optional quantification of indole compounds and more particularly of indole and skatole could be applied to numerous fields.

In the state of the art, colorimetric methods are already known for the analysis of indole derivatives mainly in liquid phase, and also instrumental methods are known which are rather more dedicated to gas phase identification and quantification of indole derivatives but which necessitate tedious steps of purification and preparation of samples.

Regarding the colorimetric methods, use is often made of p-dimethylaminobenzaldehyde (DMABA or DAB) and p-dimethylaminocinnamaldehyde (DMACA) as sensitive reagents for the detection of indole, skatole, tryptophan and other derivatives [4-6]. Recently, new colorimetric compounds containing an aldehyde function have been proposed for the detection of indole: p-methoxybenzaldehyde (MOB) and 4-methoxy-1-naphtaldehyde (MON) [7]. Although less used, croconic acid is also a reagent for the detection of indole. The molecular structure of the different compounds is illustrated in Scheme 1 below:

Scheme 1: Illustration of various reagents used for the assay of indole and the derivatives thereof

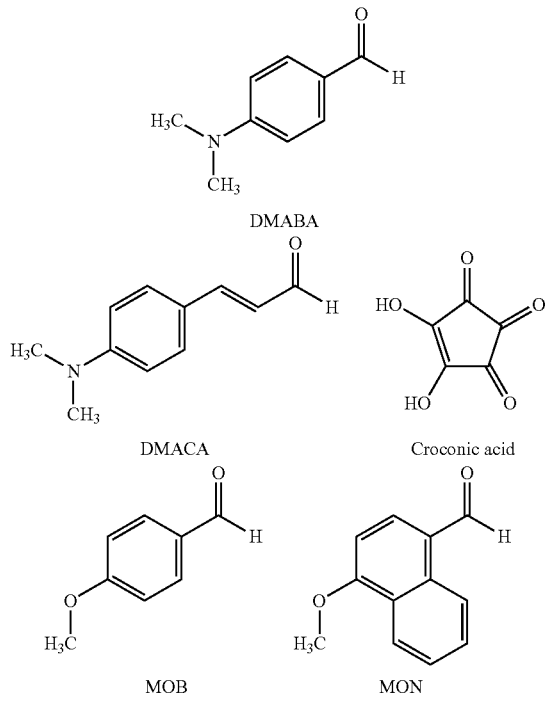

One of the major problems is the ability to assay indole, skatole or tryptophan selectively and to discriminate each of these constituents from potential interfering compounds which are often present in the same solution. The derivatives of indole effectively only differ through the type of side chain (see Scheme 2).

Scheme 2: Illustration of indole and some indole derivatives

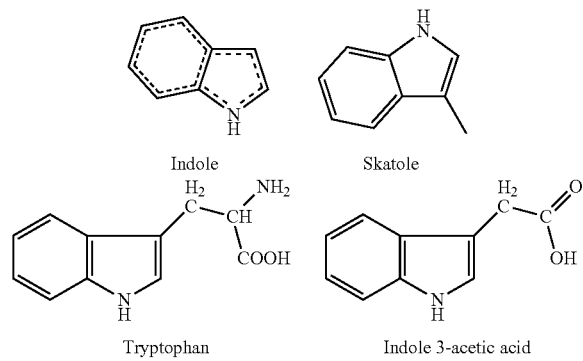

Volkl and Quadbeck used croconic acid to evidence the presence of indole and its derivatives in an aqueous solution containing about 60% concentrated sulfuric acid [8]. According to this article, the product of the reaction with indole absorbs at 495 nm with a coefficient of absorption $\epsilon=1.7\cdot10^5$ $L\cdot mol^{-1}\cdot cm^{-1}$; the product of skatole absorbs at 520 nm with a coefficient of absorption $\epsilon=1.8\cdot10^4$ $L\cdot mol^{-1}\cdot cm^{-1}$ and the product of tryptophan at 467 nm (coefficient of absorption not determined). It is therefore possible to assay indole and skatole quantitatively with respective detection limits of the order of $1\cdot10^{-6}$ and $1\cdot10^{-5}$ $mol\cdot L^{-1}$. It is also to be noted that these high coefficients of absorption restrict the dynamic measurement range over two orders of magnitude i.e. $1\cdot10^{-4}$ and $1\cdot10^{-3}$ $mol\cdot L^{-1}$ for indole and skatole respectively. The other probable interfering compounds noted by the authors are 2-methylindole (maximum absorption at 520 nm), and N-methylindole (maximum absorption at 495 nm) whose reaction products have coefficients of molecular absorption of the same order as those of indole and skatole.

The Ehrlich and Kovac reagents are prepared from DMABA diluted in an alcohol solution to which is added 10 to 20 volume % of concentrated hydrochloric acid. These reagents with indole afford a product of pink-red colour [4,5] whose maximum absorption is at 563 nm [6]. With 3-indolemethylpropionic, 3-indolepropionic and 3-indolebutyric acids they give a product of blue-red colour (575 nm) in solution after extraction with xylene [4] and of red-violet colour after two minutes' heating of the solution to be assayed containing a piece of resin on which a few drops of reagent have been deposited [9]. DMABA also produces a reaction with skatole and tryptophan. The reaction compound with skatole is formed rapidly, it is of blue-purple colour ($\lambda=578$ nm). Conversely, the compound formed by reaction with tryptophan is yellow in colour ($\lambda=460$ nm), the colouring develops very slowly (up to 24 hours) and the colouring is little intense compared with those given by the products of indole and skatole.

DMACA is also used for the detection of indole and its derivatives under conditions similar to those described for DMABA. DMACA affords a blue-green product ($\lambda_{max}=640$ nm) [5] with indole and red-violet ($\lambda=562$ nm) with large quantities of tryptophan (>2.5 $mg\cdot mL^{-1}$), with indoleacetic acid and with skatole [10].

All studies are in agreement that the tests conducted with DMACA are more sensitive than those based on a reaction with DMABA. The main advantage of these techniques based on reactions in liquid phase is the ease of conducting these tests since they entail contacting the reagents, waiting for the development of colouring and obtaining a UV-visible absorption spectrum or colorimetric measurement in order to determine concentration. However, these techniques suffer from several weak points. Regents based on DMACA, croconic acid or DMABA are not stable over time, and it is therefore necessary to prepare a new reagent solution at least every month which must be stored in a cool place and away from light. Since the development of colouring is subject to change over time, it is necessary to prepare a new standard range before each of the analyses and to observe a fixed time between the test and reading. The use of colorimetric methods is not possible if the solution to be tested is already coloured (the case often encountered in biological analysis), this often requiring an extraction step of indole derivatives using a solvent (xylene, chloroform). To conclude, despite the different preparations and probe molecules used, no study has managed to find a formulation with which it is possible to obtain a test having 100% selectivity for an indole derivative in particular, i.e. which is able to achieve substantial discrimination between different compounds.

Other detection techniques consist of using reagents adsorbed on a substrate with analytes in solution. The Vracko method consists of contacting a liquid medium containing derivatives of indole with a strip of absorbent material containing DMABA and hydrochloric acid [11]. The test is positive if pink-red colouring forms on the contact surface between the paper and the liquid to be tested. As a variant of this test, the hydrochloric acid can be replaced by oxalic acid.

These tests are not intended for conducting quantitative analyses, they just allow the detection of the presence or absence of indole. These types of strips are available commercially (Sigma-Aldrich) but the use-by date is short and very strict conditions for storage are given to users. To verify that the kits are still active, the suppliers recommend performing prior tests either with indole-producing and non-indole-producing bacteria or directly with a dilute indole solution.

Finally, other detection techniques consist of using reagents adsorbed on a substrate with analytes in gas phase. For example, the study by Kohno et al. concerns the colorimetric detection of indole in gas phase [12]. They deposited a film of Nafion containing DMABA on a polyester sheet. After exposure to indole vapours, the absorption spectrum of the film exhibits a double absorption band (535 and 580 nm) and the film is of purple colour. If the film is subsequently dipped in a 6% hydrogen peroxide solution, an intense pink-violet colour develops and the absorption bands of the product move towards the UV range (480 and 535 nm). Finally, if the film is rinsed in water and dried in dry air, the spectrum again changes to show only an intense band centred on 510 nm, when the colour of the film is magenta. This colour is stable for at least 2 h. The authors left interfering compounds to appear some with 2-methylindole and 1-methylindole and with pyrrole which give a product having a spectrum similar to that of the product with indole. On the other hand, skatole, pyridine, thiophene and the ketones do not at all interfere. The aliphatic amines, aniline and furan, give a product of yellow colour which is easily distinguishable from that of indole. The detection limit of this technique is of the order of 2 ppm indole in air at relative humidity higher than 30%. The entire duration of the 3 steps of the process is approximately 50 min. The response of the sensor to an increase in concentration is not linear but rather more parabolic between 0 and 15 ppmV. The sensitivity of the sensor is relatively constant at relative humidity values higher than 30% but drops drastically at relative humidity values lower than 20%.

International application WO 2006/107370 to Mac Donald mentions the gas phase detection of indole with the reagent DMACA adsorbed on a solid substrate [13]. The various substrates described are adsorbent paper, fabrics, plastic films, microporous films (with no other specification) of silica ($SiO_2$), of alumina, of zirconium oxide, of magnesium oxide, of titanium oxide, of iron oxide, of zinc oxide and nanoparticles of silica in powder form. The purpose in this case it is to detect the presence of indole for identifying a bacterium, but there is no quantitative measurement of the indole content in the gas phase. In addition, no study concerning interfering compounds is mentioned.

None of the conventional techniques for detecting indole is able to meet the criteria for practical analysis that is low cost, rapid, selective and sensitive. Each of the previously cited techniques has advantages and disadvantages but none meet all the criteria at the same time. In addition, none of the techniques allows gas phase or liquid phase analysis using the same device.

There is therefore a true need for a sensor at least selective for indole, that is portable (<1 kg), can be used without any particular training, capable of providing a sensitive result, of having a minimum detection limit without prior pre-concentration on the order of $1 \cdot 10^{-6}$ mol·$L^{-1}$, of giving a quick result (<15 min) and of covering the broadest possible range of detection (at least 3 orders of magnitude) without requiring the preparation of samples. In addition, this sensor must be able to be used indifferently for gas phase or liquid phase analyses, even by contact with solid or semi-solid samples. Finally, the response of this sensor must be stable over time and must not exhibit variability in response as a function of its storage time.

DESCRIPTION OF CERTAIN INVENTIVE ASPECTS

With the present invention, it is possible to solve the previously listed technical problems and to overcome the disadvantages of the prior art methods and devices.

Indeed, through their work, the inventors have designed a chemical detector of colorimetric type, which is portable, easy to handle, disposable, which can be used for indole and indole derivatives but also for other chemical compounds listed below, in gas phase and/or liquid phase and even by contact with human or animal tissue such as adipose tissue, and allows real-time trapping, detection and optionally quantification.

In addition, the chemical detector of the invention which is in solid form and more particularly in the form of a porous sol-gel material comprising one or more probe molecules, does not require the handling of a liquid except the sample if such is liquid. This characteristic of the detector of the invention allows improved storage. The detector of the invention can effectively be stored for a minimum of 6 months before use whereas the detectors of liquid reagent solution type in the prior art must be prepared at the time of analysis.

Similarly, the detector of the invention only requires the sampling of 10 to 20 µL of solution to be analysed whereas 1 to 5 mL of sample are needed in the methods of the state of the art using liquid reagents.

The present invention therefore concerns a porous sol-gel material comprising at least one probe molecule chosen from the group consisting of croconic acid and the group of probe molecule with aldehyde function consisting of p-dimethylaminobenzaldehyde (DMABA), p-dimethylaminocinnamaldehyde (DMACA), p-methoxybenzaldehyde (MOB) and 4-methoxy-1-naphtaldehyde (MON).

By <<sol-gel material>> is meant a material obtained using a sol-gel process consisting in using as precursors metal alkoxides, the same or different, of formula $M(OR)_n(R')_m$ where M is a metal such as silicon, R and R' are an alkyl group and m and n are integers with m+n=4, $2 \leq n \leq 4$ and $0 \leq m \leq 2$. The sol-gel materials are generally prepared in a solvent, which is preferably water-miscible and evaporable under gentle conditions, in which the precursors are soluble. With regard to silicon alkoxides, particular mention may be made the alcohols such as methanol, ethanol; the ethers such as diethylether and tetrahydrofuran; the chlorinated solvents such as chloroform, $CH_2Cl_2$, $C_2H_5Cl_2$ or other aprotic solvents such as $CH_3CN$, acetone, methylethylketone, or diethylene dioxide, or protic solvents such as acetic acid, formamide. In the presence of water, the hydrolysis of the alkoxide groups (—OR) occurs and these are converted to silanol groups (Si—OH) which are condensed forming siloxane groups (Si—O—Si). Small particles of size generally smaller than 1 nanometer are then formed. They aggregate and form vacancy clusters in suspension in the liquid: this is the sol. As and when polycondensation continues over time the viscosity of the sol increases until it gels: the sol becomes a gel. A solid sol-gel material is obtained by drying the gel. During this step, the residual, interstitial solvents escape from the formed polymeric network and evaporate, which causes contraction of the material. An end material is obtained whose volume is reduced compared with the volume taken up by the sol. The sol-gel can be in different forms, for example it may be prepared in a mould to impart a specific shape thereto, or it may be prepared in the form of films in particular by spin-coating or dip-coating (films having a thickness of less than 1 µm) or by spraying (films having a thickness of more than 1 µm).

The porosity of sol-gel materials allows a nomenclature to be determined in relation to pore size; indeed, according to the rules set by the International Union of Pure & Applied Chemistry (IUPAC) a distinction can be made, depending on the mean diameter of the pores in a material, between micropores (less than 20 Å), mesopores (20-500 Å) and macropores (more than 500 Å). The sol-gel material used for the present invention is porous and in particular mesoporous. Advantageously, this material has a pore-size distribution ranging from 10 to 100 angstroms, particularly 15 to 80 angstroms and more particularly from 20 to 70 angstroms and a specific surface area of 200 to 800 $m^2 \cdot g^{-1}$, in particular from 300 to 700 $m^2 \cdot g^{-1}$ and more particularly 400 to 600 $m^2 \cdot g^{-1}$ The sol-gel material used in the present invention advantageously has an intrinsic pH of less than 1 and in particular an intrinsic pH lower than 0 (i.e. negative pH). The intrinsic pH within a sol-gel material can be measured using staining reagents and in particular with thymol blue.

The sol-gel material used for the present invention is essentially prepared from 1 to 4 alkoxysilane precursors and is essentially obtained from the hydrolysis of 1 to 4 alkoxysilane precursors. The sol-gel material used for the present invention is therefore essentially formed of units derived from the hydrolysis of 1 to 4 alkoxysilane precursors. The sol-gel material can essentially be prepared from 2 or 3, and particularly from 2 different alkoxysilane precursors. As a variant, the sol-gel material can essentially be prepared from a single alkoxysilane precursor, notably of bisilane type. Irrespective of the variant, the final sol-gel material, including probe molecules, generally contains 85% and in particular 60 to 80% by weight of alkoxysilane derivatives.

In a first variant designated hereafter as $V_1$, the sol-gel material used for the present invention is essentially prepared from:
- at least one first alkoxysilane of formula $Si(OR^1)_4$ or $R^2Si(OR^3)_3$ in which $R^1$, $R^2$ and $R^3$, identical or different, represent an alkyl group with 1 to 6 carbon atoms, and
- at least one second alkoxysilane of formula $R^4Si(OR)_3$ or $(R^6O)_3Si-CH_2-CH_2-Si(OR^7)_3$ in which $R^4$ represents a substituted alkyl group with 1 to 6 carbon atoms and $R^5$, $R^6$ and $R^7$, the same or different, represent an alkyl group with 1 to 6 carbon atoms.

Advantageously, in variant $V_1$, the molar ratio of first alkoxysilane(s)/second alkoxysilane(s) is between 1:0.01 and 1:1; notably between 1:0.02 and 1:0.80; and in particular between 1:0.03 and 1:0.50.

For the radicals $R^1$, $R^2$, $R^3$, $R^5$, $R^6$ and $R^7$, by alkyl group with 1 to 6 carbon atoms is meant a straight-chain or branched alkyl group having 1 to 6 carbon atoms and in particular 1 to 4 carbon atoms.

For the $R^4$ radicals, by substituted alkyl group with 1 to 6 carbon atoms is meant a straight-chain or branched, substituted alkyl group having 1 to 6 carbon atoms and in particular 1 to 4 carbon atoms. The said $R^4$ group has one or more substitutions, identical or different, by an element chosen from the group consisting of a halogen such as fluorine or chlorine, a $-NH_2$ radical, a $-NHR^8$ radical where $R^8$ is an alkyl group with 1 to 6 carbon atoms such as previously defined, a $-COOH$ radical, a $-COOR^9$ radical where $R^9$ is an alkyl group with 1 to 6 carbon atoms such as previously defined.

As first alkoxysilane which can be used for the present invention, mention may be made of tetramethoxysilane (TMOS, $Si(OCH_3)_4$), tetraethoxysilane (TEOS, $Si(OC_2H_5)_4$), tetrapropoxysilane (TPOS, $Si(OC_3H_7)_4$), tetrabutoxysilane (TBOS, $Si(OC_4H_9)_4$), methyltrimethoxysilane (MTMOS, $(CH_3)Si(OCH_3)_3$), ethyltrimethoxysilane (ETMOS, $(C_2H_5)Si(OCH_3)_3$), propyltrimethoxysilane (PTMOS, $(C_3H_7)Si(OCH_3)_3$), methyltriethoxysilane (MTEOS, $(CH_3)Si(OC_2H_5)_3$), ethyltriethoxysilane (ETEOS, $(C_2H_5)Si(OC_2H_5)_3$) and propyltriethoxysilane (PTEOS, $(C_3H_7)Si(OC_2H_5)_3$) and the mixtures thereof. Advantageously, the first alkoxysilane used for the present invention is TMOS.

Under the present invention, the second alkoxysilane precursor allows the pore size of the sol-gel material to be modified and in particular increased through the use of different substitution groups. As second alkoxysilane which can be used for the present invention, mention may be made of 3-aminopropyltriethoxysilane (APTES, $Si(C_3H_6NH_2)(OC_2H_5)_3$), 3-aminopropyltrimethoxysilane (APTMS, $Si(C_3H_6NH_2)(OCH_3)_3$), (3-(methylamino)propyl)trimethoxysilane $(Si(C_3H_6NHCH_3)(OCH_3)_3)$, 3-carboxypropyltriethoxysilane $(Si(C_3H_6CO_2H)(OC_2H_5)_3)$, 3-carboxypropyltrimethoxysilane $(Si(C_3H_6CO_2H)(OCH_3)_3)$, 1,2-bis(triethoxysilyl)ethane $((OC_2H_5)_3Si-CH_2-CH_2-Si(OC_2H_5)_3)$, 1,2-bis(trimethoxysilyl)ethane $((OCH_3)_3Si-CH_2-CH_2-Si(OCH_3)_3)$, (3,3,3-trichloropropyl)triethoxysilane $(Si(C_2H_5Cl_3)(OC_2H_5)_3)$ and 3,3,3-trifluoropropyl-trimethoxysilane $(Si(C_2H_5CF_3)(OCH_3)_3)$ and the mixtures thereof. Advantageously, the second alkoxysilane used in the present invention is APTES.

Therefore, a particular sol-gel material used for the present invention is essentially prepared from TMOS and APTES in a molar ratio of between 1:0.01 and 1:1; notably between 1:0.02 and 1:0.80; and in particular between 1:0.03 and 1:0.50. More particularly, the TMOS/APTES molar ratio is 1:0.04 but may move up to 1:0.3. Therefore, the sol-gel material of the invention comprises units of TMOS and APTES in such proportions.

In a second variant designated hereunder as $V_2$, the sol-gel material used for the present invention is essentially prepared from at least one alkoxysilane of formula $(R^6O)_3Si-CH_2-CH_2-Si(OR^7)_3$ such as previously defined.

In a third variant designated hereunder as $V_3$, the sol-gel material used for the present invention is essentially prepared from:
- at least one first alkoxysilane of formula $(R^6O)_3Si-CH_2-CH_2-Si(OR^7)_3$ such as previously defined, and at least one second alkoxysilane of formula $Si(OR^1)_4$, $R^2Si(OR^3)_3$ or $R^4Si(OR^5)_3$ such as previously defined.

Advantageously, in the variant $V_3$, the first alkoxysilane(s)/second alkoxysilane(s) molar ratio is between 1:1 and 1:100; in particular between 1:1.25 and 1:50; and more particularly between 1:2 and 1:33.

The probe molecule used in the present invention i.e. chosen from among croconic acid and the probe molecules with aldehyde function in which DMABA, DMACA, MOB, MON, and the mixtures thereof, lies on the surface of the pores of the sol-gel material. The probe molecules can be adsorbed on the surface of the pores of the sol-gel material and/or bonded to this surface via non-covalent bonds (hydrogen bonds or ion bonds) and/or by covalent bonds. In general, the probe molecules are distributed within the entire volume of the material.

The weight percentage of the probe molecules is advantageously from 0.01 to 30%, in particular from 0.1 to 20% and more particularly from 1 to 10% relative to the total weight of the porous sol-gel material.

The porous sol-gel material may additionally contain structuring compounds such as organic polymers such as ionomers and in particular fluorinated organic polymers derived from ethylene having an acid function e.g. NAFION®, and also surfactants, generally neutral.

The present invention also concerns a method for preparing a porous sol-gel material according to the invention comprising at least one probe molecule such as previously defined.

Different preparation methods can be envisaged in the present invention. The probe molecule(s) can be incorporated in the sol-gel material after the preparation of this material using a conventional sol-gel process.

This incorporation can be made using diffusion by gas route by placing the probe molecule in gaseous form in direct contact with the material (under partial vacuum or by circulating the gas) or by liquid route by placing the material directly in a solution (aqueous or solvent) solvent) containing the probe molecule dissolved or diluted.

This incorporation can also be made by functionalization or post-doping consisting in creating a covalent bond between the material and the probe molecule. For this purpose, it is advantageous to functionalize the surface of the material to improve its compatibility with the probe molecule, or to functionalize this latter.

As a preferred variant, the preparation method according to the invention consists in adding the probe molecule directly when preparing the sol («one-pot» technique), which leads to the direct encapsulation of the probe molecule within the silica network and allows a better distribution to be obtained of the probe molecules in the sol-gel material of the present invention. The dissolving of the probe molecules can either be made in the solvent (step ($a_1$) or ($a_2$) below) or in water (step ($c_1$) or ($c_2$) below) used for preparing the sol. The preferred choice is to dissolve the probe molecule in the medium in which it is most soluble or best miscible.

According to variant ($V_1$) of the invention, the method for preparing a material comprises the following successive steps of:

$a_1$) mixing at least one first alkoxysilane of formula $Si(OR^1)_4$ or $R^2Si(OR^3)_3$ as previously defined with a solvent and at least one probe molecule chosen from the group consisting of croconic acid, DMABA, DMACA, MOB and MON;

$b_1$) adding to the mixture of step ($a_1$) at least one second alkoxysilane of formula $R^4Si(OR^5)_3$ or $(R^6O)_3Si$—$CH_2$—$CH_2$—$Si(OR^7)_3$ as previously defined;

$c_1$) adding to the mixture of step ($b_1$) water then an acid;

$d_1$) shaping the sol obtained after step ($c_1$) to obtain the sol-gel material comprising at least one probe molecule according to the invention.

The method for preparing a material, in accordance with variants ($V_2$) and ($V_3$) of the invention, comprises the following successive steps of:

$a_2$) mixing at least one first alkoxysilane of formula $(R^6O)_3Si$—$CH_2$—$CH_2$—$Si(OR^7)_3$ as previously defined with a solvent and at least one probe molecule chosen from the group consisting of croconic acid, DMABA, DMACA, MOB and MON;

$b_2$) optionally adding to the mixture of step (ad at least one second alkoxysilane of formula $Si(OR^1)_4$, $R^2Si(OR^3)_3$ or $R^4Si(OR^5)_3$ as previously defined;

$c_2$) adding to the mixture of step ($a_2$) or optionally step ($b_2$) water then an acid;

$d_2$) shaping the sol obtained after step ($c_2$) to obtain the sol-gel material comprising at least one probe molecule according to the invention.

The probe molecules used in the present invention can be dissolved, at the time of mixing at step ($a_1$) or ($a_2$) or prior to this step, in particular in the solvent used during this step. Advantageously, the probe molecules are dissolved in the solvent by placing the probe molecule/solvent mixture in an ultrasound bath for a time of 1 to 30 min, notably particular for 5 to 20 min and in particular for about 10 min (10 min±2 min) so as to obtain a homogeneous mixture. The concentration of probe molecule in the solvent may vary in relation to the needs of the detector and may reach saturation in the solvent.

The solvent used at step ($a_1$) or ($a_2$) is intended firstly to dissolve the probe molecule(s) and secondly to increase the miscibility between the precursors and water. This solvent is advantageously chosen from the group consisting of an alcohol such as methanol, ethanol, propanol or butanol, acetone, formamide, methylethylketone, chloroform, dichloromethane, acetic acid and mixtures thereof. Advantageously, this solvent is methanol and/or ethanol.

Step ($a_1$) or ($a_2$) of the method of the invention consists more particularly in mixing the first alkoxysilane(s), the solvent and the probe molecule(s) using an agitator, a magnetic agitator, magnetic stir-bar, an ultrasound bath or a homogenizer, so as to obtain a homogeneous mixture. The mixing at step ($a_1$) or ($a_2$) can be carried out at a temperature of between −45 and +30° C., notably between −35 and +10° C., in particular between −25 et 0° C. and more particularly at a temperature of the order of −15° C. (i.e. −15° C.±5° C.) for a time of 30 sec to 15 min, notably for 60 sec to 10 min, in particular from 90 sec to 5 min, and more particularly for about 2 min (i.e. 2 min±30 sec).

Advantageously, at step ($b_1$) or ($b_2$) of the method according to the invention, the adequate quantity of the second alkoxysilane(s) is added to the mixture of step (a) then the mixture obtained is agitated using an agitator, a magnetic agitator, a magnetic stir-bar, an ultrasound bath or a homogenizer, so as to obtain a homogeneous mixture. Step ($b_1$) or ($b_2$) and in particular the mixing at step ($b_1$) or ($b_2$) can be conducted at a temperature of between −45 and +30° C., notably between −35 et +10° C., in particular at between −25 and 0° C. and more particularly at a temperature of the order of −15° C. (i.e. −15° C.±5° C.) for a time of 30 sec to 15 min, notably from 60 sec to 10 min, in particular from 90 sec to 5 min, and more particularly for about 2 min (i.e. 2 min±30 sec).

Step ($c_1$) or ($c_2$) of the method according to the invention consists in adding to the mixture of step ($b_1$) or ($b_2$), firstly water, in agitating the mixture thus obtained then in adding slowly, at a rate of between 6 and 10 mL per minute, an acid such as a strong acid. The agitation at step ($c_1$) or ($c_2$) is performed using an agitator, a magnetic agitator, a magnetic stir-bar, an ultrasound bath or a homogenizer for a time of 5 sec to 5 min, notably from 10 sec to 1 min, in particular from 20 sec to 45 sec, and more particularly for about 30 sec (i.e. 30 sec±5 sec). Step ($c_1$) or ($c_2$) can be performed at a temperature of between −45 and +30° C., notably between −35 and +10° C., in particular between −25 and 0° C. and more particularly at a temperature of the order of −15° C. (i.e. −15° C.±5° C.). The water added at step ($c_1$) or ($c_2$) is advantageously ultra-pure, such as distilled water or deionized water.

The acid used at step ($c_1$) or ($c_2$) is intended to bring the probe molecules to their most reactive form, and additionally it is used as catalyst for the hydrolysis and/or polycondensation reactions of the silicon precursors. This acid is chosen from the group consisting of an organic acid such as oxalic acid, picric acid, methanesulfonic acid, n-propanesulfonic acid, trichloracetic acid, trifluoroacetic acid etc.; an inorganic acid such as hydrochloric acid, sulfuric acid, nitric acid, iodic acid, thiosulfuric acid, sulfamic acid etc.; an acid anhydride such as gaseous hydrochloric acid, maleic anhydride, succinic anhydride etc.; and the mixtures thereof. Advantageously, the acid used at step ($c_1$) or ($c_2$) is hydrochloric acid, in particular 37% hydrochloric acid and/or oxalic acid. According to one particular embodiment, the acid is added so that the pH within the matrix is less than 1, preferably less than 0. The molarity of the acid is equal to or more than 2 M, in particular equal to or more than 4 M and advantageously of the order of 6 M (i.e. 6 M±1 M) in the sol obtained at step ($c_1$) or ($c_2$).

In the method according to the invention, the molar ratio of the (first+optional second) alkoxysilanes/solvent/water is advantageously between 1:2:4 and 1:20:10, notably between 1:4:4 and 1:10:6, and in particular it is 1:5:4. The acid addition is variable and advantageously at least equal to the quantity of probe molecule(s) used and may typically reach a concentration of 8 mol·L$^{-1}$ in the sol. The use of concentrated acid is recommended to obtain the expected results. Indeed, the same addition in number of moles of a dilute acid could modify the properties of the sol-gel and contribute to the non-reproducibility of the results.

The second alkoxysilane(s) and the acid modify the initial pH conditions of the sol and catalyse gelling. Therefore, the shaping at step ($d_1$) or ($d_2$) of the method must be carried out as quickly as possible and holding the sol the closest possible to a temperature of between −45 and +30° C., notably between −35 and +10° C., in particular between −25 and 0° C. and more particularly at a temperature on the order of −15° C. (i.e. −15° C.±5° C.). Advantageously, the steps ($a_1$), ($b_1$), ($c_1$) and ($d_1$) (or ($a_2$), ($b_2$), ($c_2$) and ($d_2$)) of the method according to the invention are conducted at the same temperature. The shaping at step ($d_1$) or ($d_2$) of the method consists in depositing an adequate quantity of sol obtained at step ($c_1$) or ($c_2$) in a mould to obtain blocks of the expected sol-gel. This mould may have any shape and size. It is advantageously in polystyrene or polypropylene. For example the mould may be a well of a multi-well plate.

After step ($d_1$) or ($d_2$) of the method according to the invention and once the sol has gelled, it is also possible to carry out drying of the sol-gel blocks obtained so as to evaporate the solvents and residual acids. The drying of the sol-gel materials advantageously takes place at a controlled temperature and in a dry, inert gas atmosphere (nitrogen, argon, air, etc.). The drying of blocks of sol-gel can in particular be carried out by placing a gas-permeable cover and more particularly a porous film on the surface of the moulds, then placing these moulds at ambient temperature (i.e. 21° C.±4° C.) or in a temperature-controlled enclosure at between 10 and 60° C. and in particular at between 20 and 40° C. Drying can be conducted under an extractor hood. The drying atmosphere can also be a dry, pure inert gas (nitrogen: quality U-purity<99.5%, air: FID industrial quality, etc. . . . ). The time for complete drying varies between 2 h and 10 days and in particular between 6 h and 5 days.

Once drying is complete, the sol-gel materials of the invention, also called <<monoliths>> or <<xerogels>> herein, can be easily released from the moulds and can be stored in closed containers such as glass tubes or tubes in polytetrafluoroethylene (e.g. TEFLON®) that are hermetically sealed. For longer storage (>6 months), the dry sol-gel materials can be stored in a refrigerator at +4° C.±4° C. For even longer storage (>12 months), the sol-gel materials can be released from the mould, before complete drying, in particular when their diameter has slightly shrunk, and then stored in a sealed container such as a sealed glass tube. In this case, before using the sol-gel material of the invention as detector, the user must complete the drying of the material by placing it for a few hours, notably between 1 and 10 hours, in particular between 2 and 5 hours and typically for 3 hours in open air or in an atmosphere of dry, pure inert gas (U-quality nitrogen, industrial air for gas phase chromatography etc.). The sol-gel materials of the invention in the form of monoliths or xerogels advantageously have a thickness equal to or more than 5 μm, in particular equal to or more than 50 μm, in particular equal to or more than 200 μm and more particularly between 1 and 2 mm. The sol-gel materials of the invention must be sufficiently thick to allow absorbance measurements.

The present invention also concerns the use of a sol-gel material comprising at least one probe molecule according to the invention or able to be prepared using a preparation method according to the present invention, to trap and/or detect and optionally quantify at least one chemical compound.

The chemical compound able to be trapped and/or detected and/or quantified in the present invention is advantageously chosen from the group consisting of indole and the derivatives thereof, urobilinogen, porphobilinogen, pyrroles, primary amines and in particular aromatic primary amines, para-aminobenzoic acid, hydrazine, 4-ethoxyphenylurea (or dulcin), 5-nitro-2-propoxyaniline (or P-4000), urea nitrate, dipyrone and the derivatives of serotonin.

A <<derivative of indole>> or <<indole derivative>> in the present invention is advantageously a compound comprising an indole nucleus of formula:

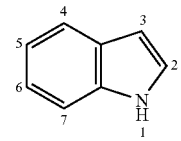

said nucleus having a least one substitution at any of the positions 2, 3, 4, 5, 6 and 7. Advantageously, said substitution(s) are chosen from the group consisting of a halogen, an alkyl group optionally substituted or a heteroalkyl group optionally substituted.

By <<optionally substituted alkyl group>> is meant a straight-chain or branched alkyl group having 1 to 6 carbon atoms, in particular 1 to 4 carbon atoms and more particularly 1 or 2 carbon atoms, optionally substituted. By <<optionally substituted heteroalkyl group>> is meant an alkyl group, optionally substituted, such as defined above also having one or more heteroatoms chosen from the group consisting of O, N, S or P.

By <<optionally substituted>> is meant one substitution or several substitutions, identical or different, on one or more carbon atoms by an element chosen from the group formed by a halogen such as fluorine or chlorine, a —$NH_2$ radical, a —OH radical, a —$NHR^8$ radical with $R^8$ representing an alkyl group with 1 to 6 carbon atoms such as previously defined, or a —COOH radical. Advantageously, the indole derivative has a single substitution and/or a substitution on carbon 2 or 3 of the indole ring. As particular examples of indole derivatives, mention may be made of skatole, tryptophan and indole 3-acetic acid, hydroxyindole.

Also, in addition to indole and the indole derivatives as explained in the <<state of the art>> section, the probe molecules used in the present invention are also known for their ability to react with other families of compounds. For example, urobilinogen whose presence in too large quantity in urines or stools can indicate pathologies such as jaundice, liver infection, cirrhosis, haematoma, etc., whereas the presence in urine of porphobilinogen which, in the presence of DMABA and sodium acetate forms a compound of red colour, indicates that the individual is suffering from porphyria.

Pyrroles with DMABA form a compound of blue/green colour with absorption between 590 and 610 nm with a view in particular to application in microbiology.

The primary amines with DMABA and DMACA form a compound of yellow colour with absorption at between 380 and 400 nm, the best sensitivity being obtained with aromatic primary amines.

Para-aminobenzoic acid reacts with DMACA to form a compound of red colour absorbing at 550 nm. Hydrazine with DMABA gives a compound of orange colour absorbing at 460 nm. The detection of this compound is of advantage in the nuclear field. Indeed, firstly, hydrazine is used as anti-corrosion agent in water for the primary and secondary circuits of nuclear plants, and secondly in the PUREX chemical waste re-processing method (Plutonium and Uranium Refining by Extraction) to separate uranium and plutonium.

4-ethoxyphenylurea (or dulcin) and 5-nitro-2-propoxyanilin (or P-4000) which are synthetic sweeteners react with DMABA. Their detection and optional quantification are of interest in the agri-food industry in which the quality control of sweeteners and notably sweeteners which may be carcinogenic for man is of importance.

Urea nitrate with DMABA and DMACA respectively forms yellow and red-coloured products without the need to add acid since urea nitrate has a strong acid nature. This detection and optional quantification is of particular interest in the field of the detection of explosives.

Dipyrone with DMACA forms an orange product in an acid medium. Its detection and optional quantification can be applied to the pharmaceutical field for verification of quality control and the infringement of analgesics, antispasmodics or antipyretics.

The derivatives of serotonin such as feruloylserotonin and p-coumaroylserotonin form with DMABA a violet-coloured product having maximum absorption at 625 nm. Their detection and quantification are of interest in the medical and pharmaceutical fields. Indeed, serotonin is found in the brain where it acts as neurotransmitter, and in the digestive system. It is involved in the regulation of functions such as thermoregulation, eating and sexual behaviour, the waking and sleeping cycle, pain, anxiety, motor control, development of the embryo. In addition, a recent study has shown that serotonin imbalance could account for 50% of crib deaths.

The MON and MOB molecules are scarcely used in analytical chemistry but especially enter into numerous compositions for hair dyeing and perfumes. In the analytical area, the use of MON has been proposed for measuring the enzymatic activity of dehydrogenase alcohol and dehydrogenase aldehyde. MOB is proposed as coloured indicator for the detection of herbicides to evaluate the resistance of weeds to these compounds. It is also used for the assay of nucleic acids or for the detection of synopathomimetic amines such as methyldopa, dopamine, noradrenalin.

Croconic acid is used for the specific assay of $Fe^{3+}$ with which it forms a coloured complex absorbing at 500 nm.

Therefore a sol-gel material comprising at least one probe molecule according to the invention or able to be prepared using a method according to the present invention to trap and/or detect and optionally quantify at least one chemical compound as previously defined can be used in the areas of biochemistry, microbiology, in the field of medical diagnosis, in the nuclear field, in the field of quality control, in the agri-food field, in the veterinary, environmental and/or health inspection field, and/or in the area of perfumes, cosmetics and/or flavourings.

More particularly, the present invention concerns a method for trapping and/or detecting and optionally quantifying at least one chemical compound such as previously defined comprising the steps of:

i) contacting a flow able to contain at least one chemical compound as previously defined with a porous sol-gel material containing at least one probe molecule as previously defined;

ii) trapping and/or detecting and optionally quantifying the chemical compound(s) which may be present.

The flow used at step (i) may be a gaseous flow or a liquid flow.

The gaseous flow used in the present invention is advantageously sampled external air (for example taken from above a field treated with pesticides) or sampled from industries in the chemical, agri-food, pharmaceutical, cosmetic or nuclear fields.

The liquid flow used in the present invention is advantageously chosen from the group consisting of a biological fluid; a plant fluid such as sap, nectar and root exudate; a food matrix; mains water, river, sea or lake water, water from air cooled towers; waste water derived in particular from intensive farming or chemical, pharmaceutical, cosmetic or nuclear industries; a pharmaceutical product; a cosmetic product; a perfume; a soil sample; etc. . . . or a mixture thereof.

A biological fluid is notably chosen from the group consisting of blood such as whole blood or anti-coagulated whole blood, blood serum, blood plasma, lymph, saliva, spit, tears, sweat, sperm, urine, stools, milk, cerebrospinal fluid, interstitial fluid, fluid taken from bone marrow, mucus or fluid from the respiratory, intestinal or genitor-urinary tract, cell extracts, tissue extracts and organ extracts. Therefore, the biological fluid may be any fluid naturally secreted or excreted by a human or animal body or any fluid recovered from a human or animal body using any technique known to one skilled in the art such as extraction, sampling or washing. The recovery and isolating steps of these different fluids from a human or animal body are performed prior to implementing the method of the invention.

Different variants can be used for the contacting at step (i) of the method according to the invention. For example, it is possible to dip the material of the invention into the liquid flow, to deposit a certain volume of liquid flow on said material, to place said material in the presence of the gas flow (static exposure) or to cause the flow in particular the gas flow to circulate over said material (dynamic exposure).

The detection at step (ii) of the invention can be performed notably by optical measurement, mass measurement (notably using a quartz balance) or acoustic measurement (notably using Love waves). Advantageously, this detection is performed by measuring the variation in absorbance, fluorescence, luminescence, mass or resonance frequency of the material according to the invention when it is exposed to a flow containing the chemical compound(s) as previously defined. If detection is performed by optical measurement, preferably the chosen wavelength is the wavelength at which the absorbance, fluorescence or luminescence of the probe molecule or of the product formed by the interaction or reaction between the probe molecule and a detected chemical compound is the highest.

The measurement obtained, compared with the measurement obtained from calibrated flows of known chemical compounds, gives direct information on the quantity and/or type of chemical compound(s) contained in the exposure flow.

Therefore, the exposures of a material according to the invention to a liquid sample may give rise to a visual or photographic observation, or via a scanner. In this case, a comparison of the intensity of the colouring developed with those previously determined at the time of calibration for a predefined range of concentrations, allows rough determination of the concentration of the chemical compound. For fine-tuned quantitative measurement, it is necessary to measure the variation in absorption at a point or over a broad spectral range as a function of contact time in order to determine the rate of formation of the coloured complex. The value of this rate is to be compared with those obtained for a standard range under the same conditions.

Finally, the present invention concerns a trapping and/or detection system comprising at least one porous sol-gel material containing at least one probe molecule according to the invention. The trapping and/or detection system according to the invention further comprises at least one element chosen from the group consisting of a millifluidic system for gas flow; an exposure chamber, optionally sealed, provided with optical windows and optionally openings for the millifluidic system in which the porous sol-gel material of the invention is placed and contacted with the flow to be analysed; a system for holding the porous sol-gel material of the invention; an irradiation device (such as a lamp, LED, laser diode, etc.); optionally an optical system for collimating and focusing the analytical light; optionally means capable of conveying the light such as optical fibres; and a detector such as a spectrometer, diode array, light-emitting diode, photodiode, interference filter, photomultiplier advantageously cooled, etc.

With regard to a method for trapping, detection and/or quantification using colorimetric comparison, the trapping and/or detection system of the invention that is used, in addition to the sol-gel material, may solely comprise an exposure chamber provided with optical windows such as a 96- or 384-multiwell plate that is flat-bottomed and transparent. The sol-gel material of the invention is deposited in the centre of a well and an adequate volume of solution to be tested (5 to 100 µL, notably 10 to 50 µL and in particular 20 µL) is deposited directly thereupon using a micropipette. After a development time identical to that used for the colorimetric calibration range, comparative reading is carried out. This development time is preferably chosen within the zone in which the reaction is almost complete i.e. generally between 10 and 60 min, notably 20 min.

For trapping, detection and/or quantification via spectral measurement, the trapping or detection system of the invention, in addition to the sol-gel material, comprises an irradiation device (lamp, LED, laser diode, etc.), optionally an optical system for collimating and focusing the analytical light, optionally means for conveying the light such as optical fibres, a detector such as a spectrometer in particular a miniature spectrometer for the visible range, OceanOptics QE65000 or any other type of detector, a diode array, photodiode, photomultiplier, etc. and an exposure chamber. As particular example of said system, the exposure chamber is formed of a multiwell plate having a transparent bottom, even transparent to the UV range (Greiner Bio-One plates, Ref. 781091 (384-well), Ref. 655087 (96-well) or Ref. 675096 (96-semiwell)). This plate is placed on an XY translation device allowing the optical beam to be brought precisely to the centre of the sol-gel material of the invention for probing over a thickness that is as homogeneous as possible. The translation plate is also provided with a liquid injection device which allows the depositing of a precise volume of liquid to be analysed into the well containing the sol-gel material. As particular example, use can be made of 384-well plates whose size is fully compatible with the size of the dry, porous sol-gel materials synthesised in 96-well plates. The sol-gel material is deposited in the centre of one well of the plate and an adequate volume of solution to be tested (from 5 to 50 µL, notably 10 to 30 µL and in particular 20 µL) is deposited directly thereupon using the liquid injection system. From this moment onwards, the successive spectra are recorded of the central area of the material (i.e. over a diameter of about 1 mm). The acquisition interval between the spectra is between 1 and 20 sec and is more particularly 1 sec (with a mean duration of the spectra of 800 ms). For precise measurement of the velocity of the reaction i.e. the slope at the point of origin corresponding to the variation in absorbance of the formed complex as a function of time, collection of the absorbance values over the first 1 to 10 minutes is largely sufficient. This time is variable depending on the concentration to be detected; the lower this concentration, the longer the acquisition time to obtain sufficiently precise measurement of absorbance. The precision of measurement will depend on the apparatus used and in particular on the signal-to-noise ratio of the diode arrays or photomultipliers used. By comparing the absorbance value measured at a given time with a previously determined calibration curve, it is possible to determine the concentration of analyte in the solution.

So that the same systems as the two particular systems presented above can be applied for gas phase analysis of chemical compounds, it is possible to use the same systems such as multiwell plates by adding a sealed cover allowing exposure of the materials to a gas flow.

For a method using a gas flow, it is possible to envisage static exposure during which the sol-gel material of the invention is simply placed in passive contact with the atmosphere containing the chemical compound(s) to be detected.

Static exposure can be carried out either in within a sealed enclosure in a predetermined volume, or in open atmosphere. The sealed enclosure may correspond to point sampling during which the concentration of chemical compound(s) has only undergone little change. This type of exposure therefore entails a step prior to step (i) of the method of the invention consisting of taking a sample. Step (i) of the method of the invention can be immediate or deferred in time after sampling (the case for laboratory analysis). Static exposure in a sealed enclosure may also correspond to exposure of the porous sol-gel material of the invention within a fixed volume in which the concentration of chemical compound(s) may increase over time (the case of a bacterial culture releasing indole). Static exposure in an open atmosphere represents the real exposure to which an individual or a thing is subjected.

In these two cases of static exposure, the detection system further requires means for holding the sol-gel material identical to the means used for determining the curve or standard colorimetric range. This trapping and/or detection system is shown in FIG. 1. Advantageously, said system comprises a fluid circuit for passing of the gas flow (1), a metal or plastic plate (2), a narrowing to block the sensor (3), the site where the sol-gel material of the invention will be placed (4), an orifice for passing of the measuring optical beam (5) and screws for securing together the 2 plates (6). This system further comprises an optical system for collimating and focusing the analytical light, means capable of conveying the light such as optical fibres, and a detector such as previously defined.

The measuring of the absorbance of the coloured complex using a said trapping and/or detection system can be performed over a wide wavelength range or it can be limited to one or two wavelengths fixed at the maximum and minimum absorption respectively of one the bands or of the absorption band of the complex in the porous sol-gel material. Finally, measurement may be colorimetric shade measurement or visual assessment of this shade.

As a variant, for the method using a gas flow, it can be envisaged to use dynamic exposure which consists of circulating, at a fixed flow rate, the atmosphere containing the chemical compound(s) to be detected directly over the porous sol-gel material of the invention. In this case, the purpose is to determine a precise concentration under identical operating conditions to those used for determining the calibration curve.

In this variant, the trapping and/or detection system of the invention advantageously comprises:
  a millifluidic system for the gas flow advantageously allowing a flow rate of 0.01 to 1.1 $L \cdot min^{-1}$;
  an exposure chamber provided with optical windows and openings for the millifluidic system (gas inlet and outlet);
  an optical system for collimating and focusing of analytical light;
  means capable of conveying the light such as optical fibres;
  a (micro)pump adapted to the desired flow rate;
  a detector such as previously defined.

Said trapping and/or detection system can be used in particular as presented below. The porous sol-gel material of the invention is deposited between the two plates as illustrated in FIG. 1 on the optical pathway. The narrowing of the millifluidic circuit allows the material to be held in the proper position. The assembly is inserted in a sample holder in Teflon equipped with two quartz optical windows. The optical inlet and outlet of the sample holder are connected via connectors of SMA type to optical fibres connected firstly to the light source and secondly to the detector. The sol-gel material is inserted in the millifluidic system. This system is placed in the exposure chamber. The gas flow is circulated in the millifluidic system for a sufficient, determined time allowing observation of notable optical variations (from a few seconds to about one hour). During the exposure time, the absorption spectrum of the sol-gel material is collected preferably at regular intervals (1 to 300 seconds) in the manner described below. The light for analysis derived from a visible lamp (tungsten) is conveyed via an optical fibre and continuously illuminates the inlet window of the chamber. The light beam, collimated by means of a lens (focal length=10 mm) and a SMA connector placed on the inlet window, comes to illuminate the sensor over a small surface area (typically of the order of 1 $mm^2$). The transmitted light is collected on the same axis via a second lens and a second SMA connector placed on the outlet window of the chamber. The transmitted light beam is conveyed via an optical fibre towards a spectrophotometer which may be miniature. An absorption spectrum of the sensor is collected at regular intervals, each acquisition lasting from 8 to 1000 msec (in particular 800 msec).

The absorbance signal of the porous sol-gel material exposed to each pollutant is acquired over a wide concentration range of the chemical compound and over a wide relative humidity range of the gas flow. On the basis of this data, calibration curves are determined for each chemical compound as a function of its concentration and the humidity of the gas flow. These calibration curves are stored in a databank which will be used for the spectral deconvolution of a spectrum of the porous sol-gel material exposed to an unknown mixture of gaseous chemical compounds.

Depending on the chosen probe molecule, it is possible to perform selective detection of a chemical compound as previously defined, and in particular of an indole derivative, and to avoid the interference of the others by choosing the best probe molecule among the list of five probe molecules used in the present invention (namely DMACA, DMABA, MON, MOB or croconic acid).

In addition, by acting on the synthesis parameters of the sol-gel material and the method of incorporating the probe molecule, it is possible to adapt the size of the pores to the size of the analyte to be detected, and hence to carry out a second <<screening>> of the hampering interfering compounds. The experimental part below proposes an example of a porous sol-gel material which is insensitive to tryptophan which is unable to enter the pores of the material, allowing the detection and distinguishing of indole and skatole. This point is important since indole and skatole are formed from tryptophan in biological media. Tryptophan is an important interfering compound in microbiology.

Similarly, by modifying the conditions of synthesis or concentration of the probe molecule incorporated in the material, it is possible to move the detection range of the lowest concentrations towards the highest concentrations by globally maintaining a range of response linearity over 3 orders of magnitude (by default, from $1 \cdot 10^{-6}$ to $1 \cdot 10^{-3}$ mol·L$^{-1}$ of indole). DMACA allows good discrimination between skatole and indole but the sensitivity threshold is obtained with a concentration of ~$10^{-6}$ mol·L$^{-1}$. DMABA, which is more soluble in alcohol, can be incorporated in larger quantities in the sol-gel material and therefore allows a higher level of sensitivity to be reached. It is therefore possible for example to use a kit with these two probe molecules in a mixture in one same sol-gel material or in two separate sol-gel materials to facilitate reading by the naked eye (the colours of the probe molecules are therefore not superimposed for the user), to obtain selectivity and sensitivity.

In addition, the formation of the coloured complex is about 3 times faster in the pores of the material than in liquid phase. With regard to indole and some of its derivatives, said complex is an azafulvenium salt, tryptophan does not form such a complex. With the method of the invention, this complex is the only one formed whereas in liquid phase a $2^{nd}$ reaction product may be formed from the $1^{st}$ complex with the addition of a $2^{nd}$ molecule of indole. In the literature, the $2^{nd}$ reaction is not taken into account in the liquid phase assay, and leads to systematic errors of estimation of indole concentrations. The azafulvenium salt formed is stable in the sol-gel material since the $2^{nd}$ reaction does not take place.

Other characteristics and advantages of the present invention will become further apparent on reading the following examples given as an illustration and which are non-limiting.

DETAILED DESCRIPTION OF CERTAIN ILLUSTRATIVE EMBODIMENTS

Figure 1:
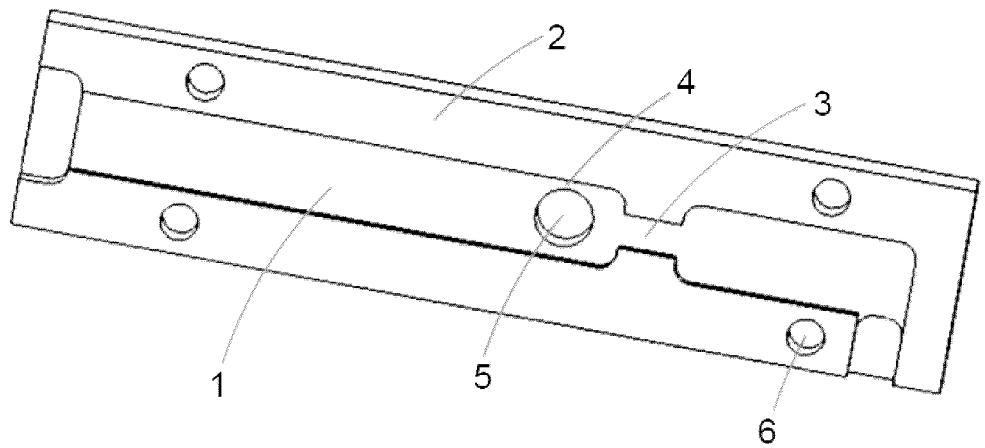
FIG. 1 gives a diagram of one of the two sides of the holder device for a porous sol-gel material containing at least one probe molecule according to the invention allowing exposure thereof to a gas sample and absorption measurements.

I. Preparation of a Mesoporous Matrix According to the Present Invention

I.1. Material Used.

The different samples of mesoporous matrices were synthesised from two precursors, TMOS and APTES. The solvent and the acid used for this synthesis were methanol and 37% hydrochloric acid (12 mol·L$^{-1}$) respectively. The described protocol uses DMACA as probe molecule.

More specifically, for preparation of 20 mL of sol doped <<to saturation>> with DMACA and with an HCl concentration of 6 mol·L$^{-1}$, the following are used:

TMOS (Fluka, ref. 09324): 3.4 mL;

methanol (Fluka, ref. 87680)+DMACA (Sigma-Aldrich, ref. 156477): 4.7 mL+70 mg;

APTES (Aldrich, ref. 440140): 0.2 mL;

ultrapure water: 1.7 mL hydrochloric acid 12 mol·L$^{-1}$: 10 mL.

I.2. Preparation of the Sol.

The first step of synthesis consists in using a magnetic agitator to mix TMOS and methanol containing the dissolved DMACA for 2 min in a Pyrex beaker placed in a bath at −15° C.±5° C. (ethanol/carbonic ice mixture or ethanol/liquid nitrogen). The desired quantity of APTES is then added to the mixture using a micropipette. After further agitation for 2 additional min, the deionized water is added. After 30 sec agitation, the slow addition of hydrochloric acid is carried out followed by shaping of the matrices.

I.3. Shaping and Drying of the Sol-Gel Matrices.

NH$_2$TEOS and hydrochloric acid modify the initial pH conditions of the sol and catalyse gelling; shaping must therefore take place as quickly as possible, the sol temperature being held the closest possible to −15° C.±5° C.

Using a micropipette, the adequate volume of sol is placed in a 96-well plate preferably in polystyrene (Greiner Bio-one, Elisa-microplates flat bottom, ref. 655001) or in polypropylene (Greiner Bio-one, Elisa-microplates flat bottom, ref. 655201). It is to be noted that to prevent compounds in or on the plates from polluting the monoliths, the plates are pretreated which comprises heating in an oven to 50° C. for 24 h renewing the atmosphere in the oven three times throughout this period (replacement with quality U nitrogen, FID quality industrial air, etc.).

Volumes of 50 to 100 µL give dry matrices of suitable thickness (400-800 µm). The shrinkage factor is between 12 and 16 for a starting sol such as the one described under part I.1. Once the sol is gelled, the multiwell plate is covered with an adhesive, microporous film (Gas permeable adhesive seals, ABGene, ref. AB-0718). The plate thus sealed is left at ambient temperature under a hood (possible release of acid vapours throughout drying) until complete dryness i.e. generally for 3 days (approximate temperature=22° C., mean relative humidity=55%).

After drying, the mean diameter of the monoliths is 2.9±0.2 mm. Once drying is complete the matrices can easily be released from the mould and can be stored in hermetically sealed glass tubes.

The protocol presented here can be adapted to the other probe molecules or mixtures thereof.

II. Characterization of the Porous Matrix According to the Invention

II.1. Porosity

II.1.1. Reminders.

It is necessary to obtain two fundamental physical characteristics i.e. the specific surface area of the material and the distribution of pore size. These two parameters together give information on the diffusion and trapping of pollutants within the materials.

The measurement of the specific surface area and of the porosity of a material is generally carried out from experimental determination of the physical adsorption isotherm of an inert gas on the surface of the material.

The Brunauer-Emmett-Teller (BET) method is the most widely used analytical method for determining the specific surface area of a solid material.

The DFT method allows determination of the density profile at equilibrium by minimizing the free energy potential, irrespective of the position of the molecule on the surface or in a pore. On the basis of this profile, it is then possible to give a precise structure to a fluid confined in a pore.

II.1.2. Measurement and Comparison with Non-Doped Matrices a) Non-Doped Matrix (as Comparison)

The non-doped matrix used for comparison is a matrix prepared as under part 1.1 but without DMACA and without acid.

b) Degassing

The xerogel to be analysed is ground to a fine powder in a mortar. In both cases, monoliths having equivalent central thicknesses (220 µm) were chosen. Since the degassing operation must be conducted with the greatest care possible, two successive degassing operations were performed. The first, vacuum degassing provides for <<rough>> degassing. The sample is heated to 100° C. and it is waited until the vacuum stabilizes at a pressure of the order of 5·10$^{-2}$ Torr (i.e. about 4 h). The second degassing is then performed directly on the degassing port of an Autosorb-1 porosimeter (Quantachrome). The temperature is set at 150° C. and it is waited until the pressure stabilizes at 5·10$^{-3}$ Torr (i.e. again about 4 h). The rise in temperature facilitates degassing of the organic molecules and of water.

During this first degassing, it was noted that initially the doped xerogel powder was white and opaque (due to light scattering) and that its colour changed throughout degassing to an opaque bright orange. This observation leads to believing that the protonated DMACA probe molecules are deprotonated during degassing and that they remain enclosed in the pores whose mouths are too small to allow the release of the DMACA even under conditions of high pressure and temperature. It can therefore be assumed that at the time of measurement the probe molecules will not leave the matrix when placed in contact with the medium to be analysed.

c) Measurement

The isotherms were determined using an Autosorb-1 porosimeter (Quantachrome) allowing the use of nitrogen gas at its normal liquefaction temperature (77K) as adsorption gas.

Adsorption-Desorption Isotherms

Figure 2:
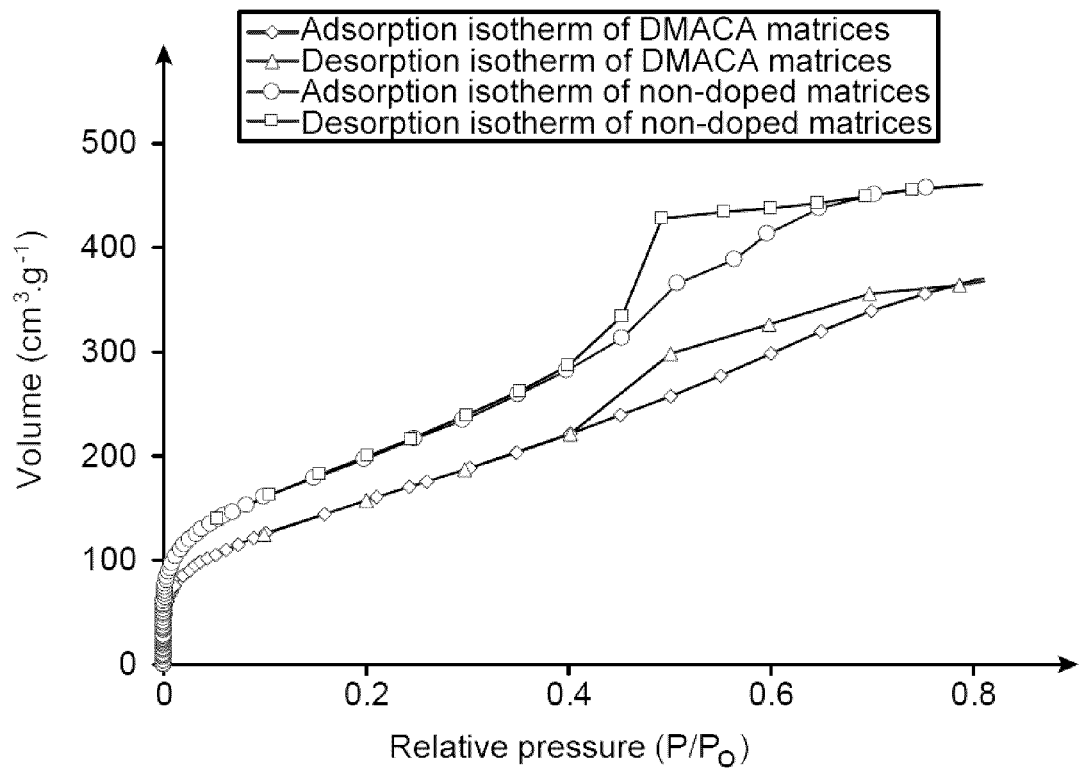
FIG. 2 illustrates the adsorption (○) and desorption (□) isotherms of nitrogen at 77 K on non-doped matrices and on saturation-doped DMACA-doped matrices, (adsorption ◇ and desorption △) according to the invention.

FIG. 2 gives the adsorption and desorption isotherms obtained firstly from saturation-doped matrices doped with DMACA in the solvent, and secondly from non-doped matrices.

The presence of micropores is detected by the strong increase in adsorbed volume at the very low relative pressures of N$_2$. The existence of mesopores is evidenced by the presence of a hysteresis loop at a relative pressure of more than 0.4. In addition, the shape of the hysteresis loop gives information on the type of interconnection. In the case in hand we are in the presence of interconnected mesopores.

The appearances of the isotherms of the doped and non-doped matrices are similar but it can be noted that the free porous volume is smaller when the pores contain DMACA.

Distribution of Pore Size

Figure 3A:
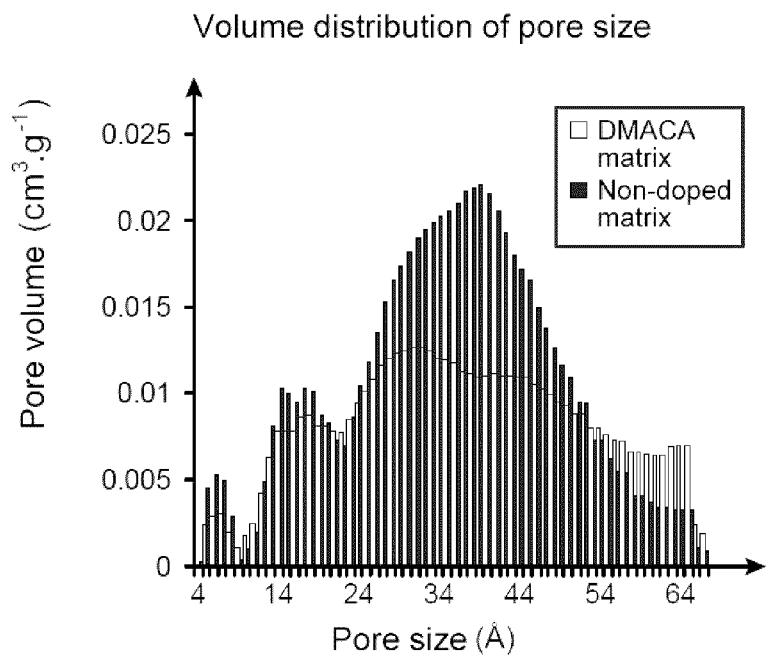
FIG. 3 gives graphs showing the contribution of pores of different sizes to the porous volume (on the left) and to the specific surface area (on the right). The non-doped matrices are shown in black (■) and the DMACA-doped matrices in white (□). The results were obtained using the DFT computing method (Neimark A. V., Ravikovitch P. I., Vishnyakov A., "Bridging scales from molecular simulations to classical thermodynamics: density functional theory of capillary condensation in nanopores", J. Phys.: Condens. Matter, vol. 15, pp. 347-365, 2003).
Figure 3B:
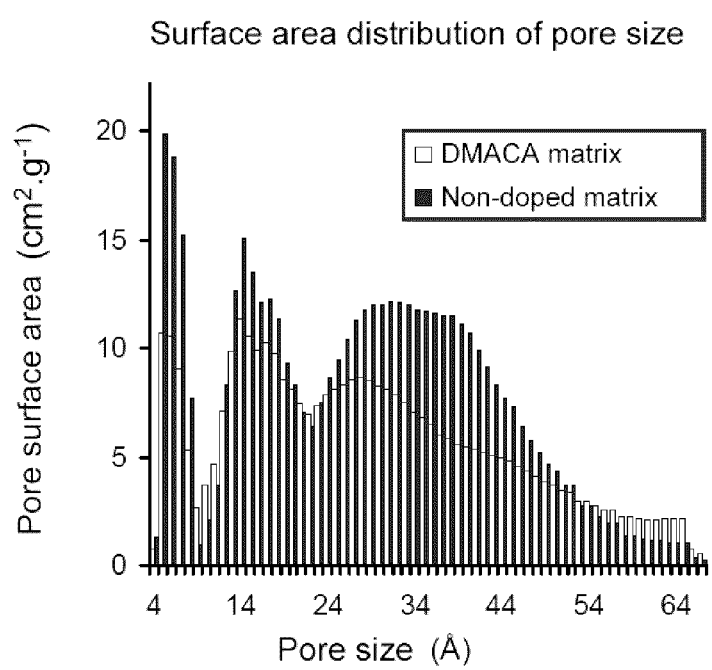

Pore size distribution can be determined in two different manners, either size distribution contributing to porous volume or size distribution contributing to specific surface area. The histograms shown in FIG. 3 show these two types of distribution.

It is noted, according to the conclusions drawn from the study of the adsorption-desorption isotherms, that the two matrices have a small population of micropores with diameter less than 20 Å and a large population of mesopores with a diameter here of between 20 and 70 Å. In addition, it is to be noted that the mesopores contribute towards total porous volume and surface area to the proportion of about 85% and 64% respectively for the two types of matrices examined. The entirety of the preceding results is summarized in Table 1 below.

TABLE 1

Comparison of specific surface areas and porous volumes of a non-doped matrix and a matrix doped with concentrated DMACA

|  | Non doped matrix | DMACA-doped matrix "to saturation" |
|---|---|---|
| $S_{spec\,BET}$ (m$^2$·g$^{-1}$) | 760 ± 32 | 610 ± 30 |
| $S_{micropores}$ (m$^2$·g$^{-1}$) | 170 ± 7 | 130 ± 7 |
| $V_{por\,total}$ (cm$^3$·g$^{-1}$) | 0.673 | 0.523 |

II.3. Conclusions.

The method according to the invention using strong concentrations of acid allows the incorporation, in sol-gel synthesis, of a large quantity of protonated probe molecules.

The results of the characterization tests prove that the operating conditions used here allow the storage of a porous matrix having a specific surface area and pore size distribution compatible with the size of the analytes to be detected (indole, skatole). In addition, the synthesis time (20 min) which includes the preparation of the sol and the gelling time of the material remains compatible with an industrialisation step. The drying step may last 24 h if the gel pellets are released from the mould immediately after gelling or 3 days if the material is stored in its container.

To conclude, the use of multiwell plates (96 wells) allows matrices to be obtained of reproducible size and shape (discs 2.9 mm in diameter and of thickness varying between 400 to 800 μm in relation to the volume of sol used when filling the wells) inducing the lowest possible inter-batch variability.

III. Use of the Doped Matrices According to the Invention

To illustrate the advantage of the invention, detection measurements are given below for two probe molecules.

III.1. Gas Phase and Liquid Phase Colorimetric Tests

III.1.1. Exposure to Indole-Containing Solutions

For each probe molecule (DMACA or DMABA), 12 matrices containing the optimal concentration of reagent (saturation of the probe molecule solution) and 12 matrices containing the same reagents at a concentration 5 times weaker were synthesized following the method such as described under point 1.2. The volumes in μL (70, 80 and 90) correspond to the initial volumes of sol poured into the wells. After gelling of the sol and drying of the matrices, the thicknesses of the matrices obtained are proportional to the initial volumes of sol. Four indole solutions at different concentrations ($10^{-6}$, $10^{-5}$, $10^{-4}$ and $10^{-3}$ mol·L$^{-1}$) were prepared. Twenty μL of each solution were deposited in 6 wells differing through the concentration of the probe molecule and the thickness of the matrix.

Figure 4:
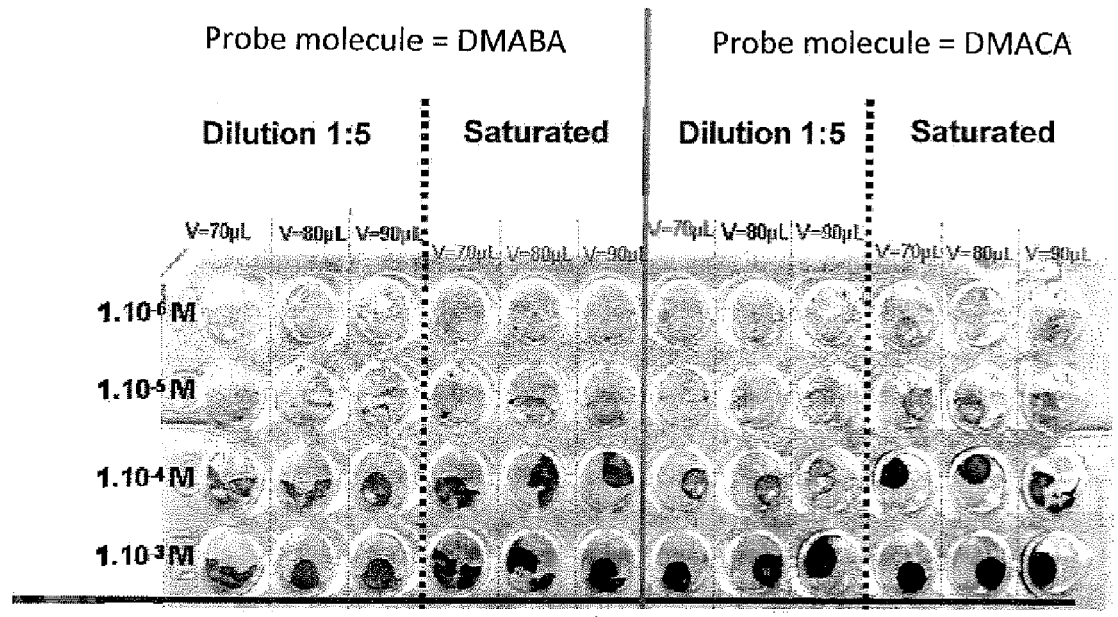
FIG. 4 gives the results of colorimetric tests for the assay of indole in different porous matrices doped with DMACA and DMABA according to the invention.

It is seen in FIG. 4 that, for one same indole concentration, the thicker the matrices the more intense the colouring (red when the probe molecule is DMABA and green when the probe molecule is DMACA). In addition, the colouring also becomes more intense when the concentration of indole increases. These results are expected since the absorbance of the products, in this case azafulvenium salts, is proportional to the optical pathway (thickness of the matrix) and to the concentration of product derived from the reaction of indole with protonated DMABA or DMACA present in excess in the matrix.

One of the most important points of these experiments is the sensitivity which can be obtained for a visual test by means of the change of colour within the visible range, which is $10^{-6}$ mol·L$^{-1}$ for indole.

III.1.2. Exposure to Solutions Containing Skatole or Tryptophan

In similar manner to previously, if liquid solutions containing skatole or tryptophan are caused to react with sensors doped with DMACA or DMABA, the following colour changes are obtained:

DMACA sensor and skatole→change from pale orange to violet

DMACA sensor and tryptophan→no change in colouring (remains pale orange)

DMABA sensor and skatole→change from yellow to violet

DMACA sensor and tryptophan→no change in colour (remains yellow)

It can be concluded from this experiment that the sensors doped with DMACA or DMABA prepared as described under point I.2 do not react with the potential interfering compound i.e. tryptophan when measurements are taken.

In addition, it appears that the discrimination between skatole and indole is possible using this method since the products formed have distinctly different colours: with DMACA respectively violet and green; with DMABA respectively violet and pink.

III.2. Exposure to a Range of Indole Concentrations in Liquid Phase

Figure 5A:
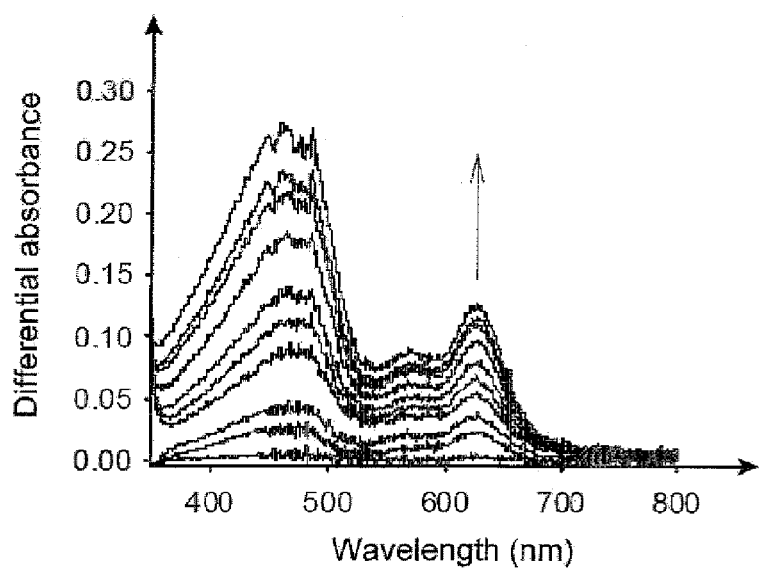
FIG. 5A shows the spectral changes observed over time on the addition of 20 μL of an indole solution in a sol-gel matrix doped with DMACA according to the invention.

The example below shows the results obtained when exposing a sensor doped with DMACA (20% saturation in methanol—Thickness=800 μm) to 20 μL of an indole solution at $6.3 \cdot 10^{-5}$ mol·L$^{-1}$, deposited directly on the sensor. FIG. 5A illustrates the spectral changes of the sensor over time and FIG. 5B shows the evolution in absorption difference at the wavelength of 624 nm.

Figure 5B:
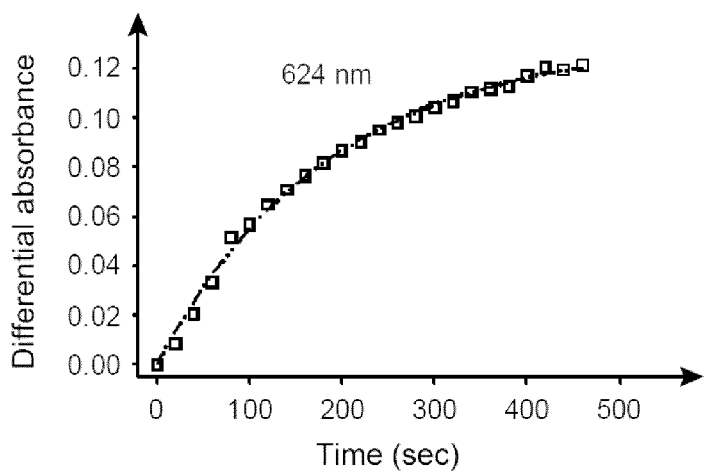
FIG. 5B shows the formation kinetics of the coloured complex at 624 nm.
Figure 6:
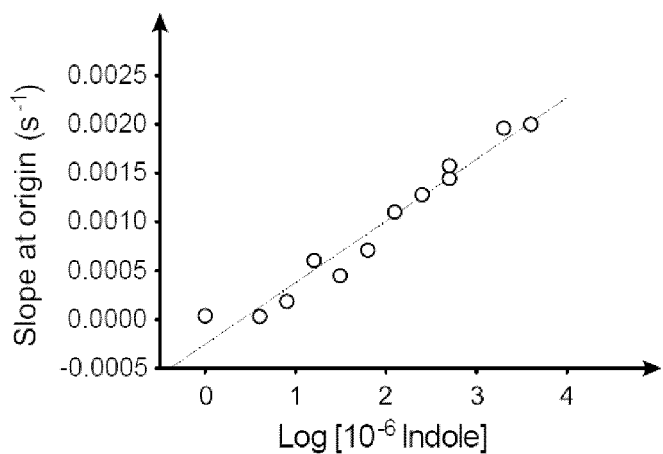
FIG. 6 shows the calibration curve for the detection of indole in a liquid medium. The X-axis corresponds to the logarithm of indole concentration (between $10^{-6}$ and $10^{-3}$ mol·L$^{-1}$) and the Y-axis to the rate of formation of the coloured complex.

By determining the value of the slope at the origin i.e. the initial reaction rate in the graph in FIG. 5B and repeating this same operation for different concentrations of indole, it is possible to plot a calibration curve such as shown in FIG. 6.

III.3. Exposure in Gas Phase

The exposure of a DMACA-doped matrix to indole in gas phase induces the same spectral changes as in liquid phase (see FIG. 5).

Figure 7:
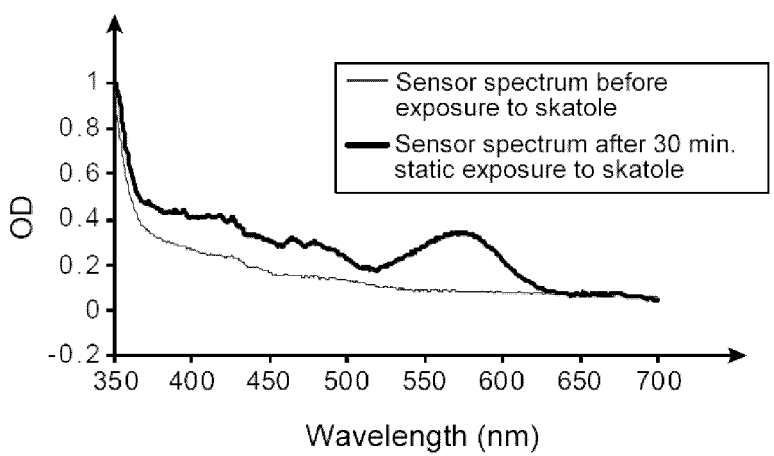
FIG. 7 illustrates the spectral variation obtained when exposing a DMACA-doped matrix according to the invention to skatole vapours.

One example of exposure to skatole in gas phase is shown in FIG. 7. The complex formed by the reaction of skatole with DMACA is practically not absorbed at 624 nm, the wavelength corresponding to the maximum absorption of the complex formed with indole. It is therefore easy to discriminate between the two pollutants and to obtain a quantitative measurement of each constituent in a mixture.

REFERENCES

[1] Japanese patent application 2006258803 by Tatsuya published on Sep. 28, 2006.
[2] Article by Wood et al., 2003, Mycologica, vol. 95(5), pages 807-808.
[3] Article by Curioni and Bosset, 2002, International Dairy Journal, vol. 12, pages 959-984.
[4] Article by Lombard and Dowell, 1983, Journal of Clinical Microbiology, vol. 18(3), pages 609-613.
[5] Article by Miller and Wright, 1982, Journal of Clinical Microbiology, vol. 15(4), pages 589-592.
[6] Article by Turner, 1961, Biochemical Journal, vol. 78, pages 790-792.
[7] Article by Kohno et al., 2009, Analytical Sciences, vol. 25, pages 129-132.
[8] Article by Volkl and Quadbeck, 1973, Arztl. Lab., vol. 19, pages 535-536.
[9] Article by Qureshi and Qureshi, Analytical Chemistry, vol. 38(13), pages 1956-1958.
[10] Article by Durkee and Stirbois, Journal of Chromatology, vol. 13, pages 173-180.
[11] Article by Vracko and Sherris, 1963, American Journal of Clinical Pathology, vol. 39, pages 429-432.
[12] Article by Kohno et al., 2007, Chemistry Letters, vol. 36(1), pages 98-99.
[13] International publication WO 2006/107370 to Mac Donald published on Oct. 12, 2006.

What is claimed is:

1. A porous sol-gel material comprising at least one probe molecule selected from the group consisting of croconic acid, p-dimethylaminobenzaldehyde (DMABA), p-dimethylaminocinnamaldehyde (DMACA), p-methoxy-benzaldehyde (MOB) and 4-methoxy-1-naphtaldehyde (MON) wherein said sol-gel material has an intrinsic pH lower than 1 and notably an intrinsic pH lower than 0,
wherein said sol-gel material is prepared:
(1) from a mixture comprising:
at least one first alkoxysilane of formula $Si(OR^1)_4$ or $R^2Si(OR^3)_3$ wherein $R^1$, $R^2$ and $R^3$, identical or different, are an alkyl, maw with 1 to 6 carbon atoms, and
at least one second alkoxysilane of formula $R^4Si(OR^5)_3$ or $(R^6O)_3Si-CH_2-CH_2-Si(OR^7)_3$ wherein $R^4$ is a substituted alkyl group with 1 to 6 carbon atoms, and $R^5$, $R^6$ and $R^7$, identical or different, are an alkyl group with 1 to 6 carbon atoms;
with the molar ratio of first alkoxysilane(s)/second alkoxysilane(s) is between 1:0.01 and 1:1; or
(2) from at least one alkoxysilane of formula $(R^6O)_3Si-CH_2-CH_2-Si(OR^7)_3$ wherein $R^6$ and $R^7$, identical or different, are an alkyl group with 1 to 6 carbon atoms; or
(3) from a mixture comprising:
at least one first alkoxysilane of formula $(R^6O)_3Si-CH_2-CH_2-Si(OR^7)_3$ wherein $R^6$ and $R^7$, identical or different, are an alkyl, maw with 1 to 6 carbon atoms, and
at least one second alkoxysilane of formula $Si(OR^1)_4$, $R^2Si(OR^3)_3$ or $R^4Si(OR^5)_3$ wherein $R^1$, $R^2$ and $R^3$, identical or different, are an alkyl, maw with 1 to 6 carbon atoms, $R^4$ is a substituted alkyl group with 1 to 6 carbon atoms, and $R^5$ is an alkyl group with 1 to 6 carbon atoms;
with the molar ratio of first alkoxysilane(s)/second alkoxysilane(s) is between 1:1 and 1:100;
wherein $R^4$ is an alkyl group with 1 to 6 carbon atoms substituted by one or more elements chosen from the group consisting of a halogen, a $-NH_2$ radical, a $-NHR^8$ radical where $R^8$ is an alkyl group with 1 to 6 carbon atoms, a $-COOH$ radical, a $-COOR^9$ radical where $R^9$ is an alkyl group with 1 to 6 carbon atoms.

2. The sol-gel material according to claim 1, wherein said first alkoxysilane of formula $Si(OR^1)_4$ or $R^2Si(OR^3)_3$ is selected from the group consisting of tetramethoxysilane (TMOS, $Si(OCH_3)_4$), tetraethoxysilane (TEOS, $Si(OC_2H_5)_4$), tetrapropoxysilane (TPOS, $Si(OC_3H_7)_4$), tetrabutoxysilane (TBOS, $Si(OC_4H_9)_4$), methyltrimethoxysilane (MTMOS, $(CH_3)Si(OCH_3)_3$), ethyltrimethoxysilane (ETMOS, $(C_2H_5)Si(OCH_3)_3$), propyltrimethoxysilane (PTMOS, $(C_3H_7)Si(OCH_3)_3$), methyltriethoxysilane (MTEOS, $(CH_3)Si(OC_2H_5)_3$), ethyltriethoxysilane (ETEOS, $(C_2H_5)Si(OC_2H_5)_3$), propyltriethoxysilane (PTEOS, $(C_3H_7)Si(OC_2H_5)_3$) and mixtures thereof.

3. The sol-gel material according to claim 1, wherein said second alkoxysilane of formula $R^4Si(OR^5)_3$ or $(R^6O)_3Si-CH_2-CH_2-Si(OR^7)_3$ is selected from the group consisting of 3-aminopropyltriethoxysilane (APTES, $Si(C_3H_6NH_2)(OC_2H_5)_3$), 3-aminopropyltrimethoxysilane (APTMS, $Si(C_3H_6NH_2)(OCH_3)_3$), (3-(methylamino)propyl)trimethoxysilane ($Si(C_3H_6NHCH_3)(OCH_3)_3$), 3-carboxypropyltriethoxysilane ($Si(C_3H_6CO_2H)(OC_2H_5)_3$), 3-carboxypropyltrimethoxysilane ($Si(C_3H_6CO_2H)(OCH_3)_3$), 1,2-bis(triethoxysilyl)ethane ($(OC_2H_5)_3Si-CH_2-CH_2-Si(OC_2H_5)_3$), 1,2-bis(trimethoxysilyl)ethane ($(OCH_3)_3Si-CH_2-CH_2-Si(OCH_3)_3$), (3,3,3-trichloropropyl)triethoxysilane ($Si(C_2H_5CCl_3)(OC_2H_5)_3$) and 3,3,3-trifluoropropyl-trimethoxysilane ($Si(C_2H_5CF_3)(OCH_3)_3$) and mixtures thereof.

4. A method for preparing a porous sol-gel material according to claim 1, comprising the following successive steps of:
$a_1$) mixing at least one first alkoxysilane of formula $Si(OR^1)_4$ or $R^2Si(OR^3)_3$ wherein $R^1$, $R^2$ and $R^3$, identical or different, are an alkyl group with 1 to 6 carbon atoms, with a solvent and at least one probe molecule selected from the group consisting of croconic acid, DMABA, DMACA, MOB and MON;
$b_1$) adding to the mixture of step ($a_1$) at least one second alkoxysilane of formula $R^4Si(OR^5)_3$ or $(R^6O)_3Si-CH_2-CH_2-Si(OR^7)_3$ wherein $R^4$ is a substituted alkyl group with 1 to 6 carbon atoms and $R^5$ is an alkyl group with 1 to 6 carbon atoms, and wherein $R^6$ and $R^7$, identical or different, are an alkyl group with 1 to 6 carbon atoms;
$c_1$) adding to the mixture of step ($b_1$) water and then an acid;
$d_1$) shaping the sol obtained after step ($c_1$) to obtain the sol-gel material containing at least one probe molecule.

5. A method for preparing a porous sol-gel material according to claim 1, comprising the following successive steps of:
$a_2$) mixing at least one first alkoxysilane of formula $(R^6O)_3Si-CH_2-CH_2-Si(OR^7)_3$ wherein $R^6$ and $R^7$, identical or different, are an alkyl group with 1 to 6 carbon atoms with a solvent and at least one probe molecule selected from the group consisting of croconic acid, DMABA, DMACA, MOB and MON;
$b_2$) optionally adding to the mixture of step ($a_2$) at least one second alkoxysilane of formula $Si(OR^1)_4$, $R^2Si(OR^3)_3$ or $R^4Si(OR^5)_3$ wherein $R^1$, $R^2$ and $R^3$, identical or different, are an alkyl group with 1 to 6 carbon atoms, $R^4$ is a substituted alkyl group with 1 to 6 carbon atoms, and $R^5$ is an alkyl group with 1 to 6 carbon atoms;

c$_2$) adding to the mixture of step (a$_2$) or optionally of step (b$_2$) water and then an acid;

d$_2$) shaping the sol obtained after step (c$_2$) to obtain the sol-gel material containing at least one probe molecule.

6. The method according to claim 4, wherein said solvent is selected from the group consisting of an alcohol such as methanol, ethanol, propanol or butanol, acetone, formamide, methylethylketone, chloroform, dichloromethane, acetic acid and mixtures thereof.

7. The method according to claim 4, wherein said acid is selected from the group consisting of an organic acid, an inorganic acid and an acid anhydride.

8. The method according to claim 4, wherein the molar ratio of the first+optional second alkoxysilane(s)/solvent/water is advantageously between 1:2:4 and 1:20:10, notably between 1:4:4 and 1:10:6, and in particular it is 1:5:4.

9. The method according to claim 5, wherein said solvent is selected from the group consisting of an alcohol such as methanol, ethanol, propanol or butanol, acetone, formamide, methylethylketone, chloroform, dichloromethane, acetic acid and mixtures thereof.

10. The method according to claim 5, wherein said acid is selected from the group consisting of an organic acid, an inorganic acid and an acid anhydride.

11. The method according to claim 5, wherein the molar ratio of the first+optional second alkoxysilane(s)/solvent/water is advantageously between 1:2:4 and 1:20:10, notably between 1:4:4 and 1:10:6, and in particular it is 1:5:4.

12. A method for trapping and/or detecting and optionally quantifying at least one chemical compound comprising the steps of:

i) contacting a flow able to contain at least one chemical compound with a porous sol-gel material containing at least one probe molecule such as defined in claim 1; and ii) trapping and/or detecting and optionally quantifying the chemical compound(s) which may be present.

13. The method according to claim 12, wherein said chemical compound is selected from the group consisting of indole and its derivatives, urobilinogen, porphobilinogen, pyrroles, primary amines and in particular the aromatic primary amines, para-aminobenzoic acid, hydrazine, 4-ethoxyphenylurea (or dulcin), 5-nitro-2-propoxyaniline (or P-4000), urea nitrate, dipyrone, the derivatives of serotonin, the synopathomimetic amines, herbicides, nucleic acids and $Fe^{3+}$.

14. The method according to claim 12, wherein the said flow is a gas flow or a liquid flow.

15. The method according to claim 12, wherein the detection at step (i) is conducted by measuring the variation in absorbance, fluorescence, luminescence, mass or resonance frequency of said porous sol-gel material when it is exposed to a flow containing the chemical compound(s).

16. A trapping and/or detection system comprising at least one porous sol-gel material containing at least one probe molecule according to claim 1.

17. The trapping and/or detection system according to claim 16, wherein it further comprises at least one element selected from the group consisting of a millifluidic system for gas flow; an exposure chamber optionally sealed, provided with optical windows and optionally with openings for the millifluidic system in which the porous sol-gel material is placed and contacted with the flow to be analysed; a system for holding the porous sol-gel material; an irradiation device; an optical system for collimating and focusing analytical light; means capable of conveying the light; and a detector.

18. The porous sol-gel material according to claim 1, having a pore-size distribution ranging from 15 Å to 80 Å.

19. The porous sol-gel material according to claim 18, having a pore-size distribution ranging from 20 Å to 70 Å.

* * * * *

UNITED STATES PATENT AND TRADEMARK OFFICE
CERTIFICATE OF CORRECTION

PATENT NO.       : 9,018,016 B2
APPLICATION NO.  : 13/508702
DATED            : April 28, 2015
INVENTOR(S)      : Sabine Crunaire It is certified that error appears in the above-identified patent and that said Letters Patent is hereby corrected as shown below:

In column 2 (page 1, item 56) at line 7, Under Other Publications, change "chloroindol:" to --chloroindole:--.

Page 1 (item 57, Abstract) at line 7, Change "naphtaldehyde" to --naphthaldehyde--.

In column 1 (page 2, item 56) at line 12, Under Other Publications, change "Reation" to --Reaction--.

In column 2 at line 9, Change "Emmenthal" to --Emmental--.

In column 2 at line 32 (approx.), Change "naphtaldehyde" to --naphthaldehyde--.

In column 6 at line 3, Change "naphtaldehyde" to --naphthaldehyde--.

In column 6 at line 49, Change "$m^2 \cdot g^{-1}$" to --$m^2 \cdot g^{-1}$.--.

In column 7 at line 7, Change "$R^4Si(OR)_3$" to --$R^4Si(OR^5)_3$--.

In column 9 at line 26, Change "(ad" to --($a_2$)--.

In column 10 at line 39 (approx.), Change "trichloracetic" to --trichloroacetic--.

In column 13 at line 33, Change "synopathomimetic" to --sympathomimetic--.

In column 23 at line 39, In Claim 1, change "naphtaldehyde" to --naphthaldehyde--.

In column 23 at line 46, In Claim 1, change "alkyl, maw" to --alkyl group--.

In column 23 at line 60, In Claim 1, change "alkyl, maw" to --alkyl group--.

In column 23 at line 64, In Claim 1, change "alkyl, maw" to --alkyl group--.

In column 26 at lines 9-10 (approx.), In Claim 13, change "synopathomimetic" to --sympathomimetic--.

Signed and Sealed this
First Day of March, 2016

Michelle K. Lee
*Director of the United States Patent and Trademark Office*